United States Patent
Prickaerts et al.

(10) Patent No.: US 10,357,486 B2
(45) Date of Patent: Jul. 23, 2019

(54) TREATMENT OF COGNITIVE IMPAIRMENT WITH PDE4 INHIBITOR

(71) Applicant: Universiteit Maastricht, Maastricht (NL)

(72) Inventors: Jos Prickaerts, Maastricht (NL); Marlies van Duinen, Maastricht (NL); Anke Sambeth, Holtum (NL); Arjan Blokland, Beek (NL)

(73) Assignee: UNIVERSITEIT MAASTRICHT, Maastricht (NL)

( * ) Notice: Subject to any disclaimer, the term of this patent is extended or adjusted under 35 U.S.C. 154(b) by 129 days.

(21) Appl. No.: 14/460,905

(22) Filed: Aug. 15, 2014

(65) Prior Publication Data
US 2015/0051254 A1 Feb. 19, 2015

Related U.S. Application Data

(60) Provisional application No. 61/866,643, filed on Aug. 16, 2013.

(51) Int. Cl.
*A61K 31/44* (2006.01)
*A61K 9/20* (2006.01)

(52) U.S. Cl.
CPC ............ *A61K 31/44* (2013.01); *A61K 9/2018* (2013.01)

(58) Field of Classification Search
None
See application file for complete search history.

(56) References Cited

U.S. PATENT DOCUMENTS

| | | | |
|---|---|---|---|
| 4,663,318 A | 5/1987 | Davis | |
| 4,895,841 A | 1/1990 | Sugimoto et al. | |
| 4,948,807 A | 8/1990 | Rosin et al. | |
| 5,177,085 A | 1/1993 | Naef | |
| 5,602,176 A | 2/1997 | Enz | |
| 5,606,064 A | 2/1997 | Lensky | |
| 5,712,298 A | 1/1998 | Amschler | |
| 5,985,864 A | 11/1999 | Imai et al. | |
| 6,099,863 A | 8/2000 | Gilis et al. | |
| 6,140,321 A | 10/2000 | Imai et al. | |
| 6,245,911 B1 | 6/2001 | Imai et al. | |
| 6,252,081 B1 | 6/2001 | Iimura | |
| 6,358,527 B1 | 3/2002 | Gilis et al. | |
| 6,565,883 B2 | 5/2003 | Ogorka et al. | |
| 7,148,354 B2 | 12/2006 | Reddy et al. | |
| 7,160,559 B1 | 1/2007 | McGee et al. | |
| 7,470,791 B2 | 12/2008 | Kohl et al. | |
| 7,727,548 B2 | 6/2010 | Morita et al. | |
| 7,727,552 B1 | 6/2010 | Ukai et al. | |
| 7,951,397 B2 | 5/2011 | Dietrich et al. | |
| 2006/0003989 A1 | 1/2006 | Quay et al. | |
| 2006/0183776 A9 | 8/2006 | Pratt | |
| 2008/0234486 A1 | 9/2008 | Civit et al. | |
| 2009/0136473 A1 | 5/2009 | Singh et al. | |
| 2012/0329831 A1 | 12/2012 | Fanda et al. | |

FOREIGN PATENT DOCUMENTS

| | | |
|---|---|---|
| WO | WO1991/15451 A1 | 10/1991 |
| WO | WO1994/10118 A1 | 5/1994 |
| WO | WO 1997/22584 | 6/1997 |
| WO | WO 2000/19985 | 4/2000 |
| WO | WO2001/87281 A2 | 11/2001 |
| WO | WO2002/074726 A2 | 9/2002 |
| WO | WO 2003/099334 | 12/2003 |
| WO | WO2004/080967 A1 | 9/2004 |
| WO | WO2005/061458 A2 | 7/2005 |
| WO | WO 2006/032675 | 3/2006 |
| WO | WO2006/044528 A1 | 4/2006 |
| WO | WO 2006/097456 | 9/2006 |
| WO | WO2006/110588 A2 | 10/2006 |
| WO | WO2006/135828 A2 | 12/2006 |
| WO | WO2011163469 A1 | 12/2011 |

OTHER PUBLICATIONS

Richter et al., Exp.Op.Ther.Targ., published online Jul. 25, 2013, vol. 17, No. 9, pp. 1011-1027.*
"Therapeutic window", Merriam Webster online dictionary, https://www.merriam-webster.com/medical/therapeutic%20window, accessed Jun. 20, 2017.*
Blokland et al., PDE Inhibition and cognition enhancement, Expert Opin. Ther. Patents, 22(4):349-354 (2012).
Bruno et al., GEBR-7b, a novel PDE4D selective inhibitor that improves memory in rodents at non-emetic doses, British J. Pharmacol., 164:2054-2063 (2011).
Egawa et al., Rolipram and its Optical Isomers, Phosphodiesterase 4 Inhibitors, Attenuated the Scopolamine-Induced Impairments of Learning and Memory in Rats, Jpn. J. Pharmacol., 75:275-281 (1997).
Gallant et al., Discovery of MK-0952, a selective PDE4 inhibitor for the treatment of long-term memory loss and mild cognitive impairment, Bioorganic & Medicinal Chemistry Letters 20:6387-6393 (2010).
Gong et al., Persistent improvement in synaptic and cognitive functions in an Alzheimer mouse model after rolipram treatment, J. Clin. Investigation, 114(11):1624-1634 (2004).
Huang et al., L-454,560, a potent and selective PDE4 inhibitor with in vivo efficacy in animal models of asthma and cognition, Biochem. Pharmacol. 73:1971-1981 (2007).
Jacobsen, Alzheimer's Disease: An Overview of Current and Emerging Therapeutic Strategies, Curr. Topics in Medicinal Chem., 2:343-352 (2002).
Kanes et al., Rolipram: A Specific Phosphodiesterase 4 Inhibitor with Potential Antipsychotic Activity, Neuroscience, 144(1):239-246 (Jan. 2007).

(Continued)

*Primary Examiner* — Jeffrey S Lundgren
*Assistant Examiner* — Stephanie K Springer
(74) *Attorney, Agent, or Firm* — Patent Law Works LLP

(57) ABSTRACT

This invention relates to the treatment of varying degrees of cognitive impairment associated with, for example, aging, Alzheimer's disease, schizophrenia with low dose administration of a PDE4 inhibitor, specifically roflumilast.

7 Claims, 5 Drawing Sheets

(56) References Cited

OTHER PUBLICATIONS

Lakics et al., Quantitative comparison of phosphodiesterase mRNA distribution in human brain and peripheral tissues, Neuropharmacology 59:367-374 (2010).
Li et al., Phosphodiesterase-4D Knock-Out and RNA Interference-Mediated Knock-Down Enhance Memory and Increase Hippocampal Neurogenesis via Increased cAMP Signaling, J. Neuroscience, 31(1):172-183 (Jan. 2011).
McLachlan et al., Archives of Neurology 64:456-457 (2007).
NHS UK National Research Ethics Service Research Summaries Register, 2013, Effect of Roflumilast on cognitive function in schizophrenia (Aug. 2013).
NHS UK National Research Ethics Service Research Summaries Register, 2013, fluilast to reduce Ketamine-Induced Cognitive Deficits (Aug. 2013).
NHS UK National Research Ethics Service Research Summaries Register, 2013, A PET Study to Determine PDE4 Occupancy of fluilast (Aug. 2013).
NHS UK National Research Ethics Service Research Summaries Register, 2013, Roflumilast-Donepezil to reverse scopolamine induced cognitive deficit (Aug. 2013).
Prickaerts., Phosphodiesterase Inhibitors, Encyclopedia of Psychopharmacology, ed Stolerman I P Springer Veriag pp. 1022-1028 (2010).
Reneerkens et al., Selective phosphodiesterase inhibitors: a promising target for cognition enhancement, Psychopharmacology 202:419-443 (2009).
Rodefer et al., Selective phosphodiesterase inhibitors improve performance on the ED/ID cognitive task in rats., Neuropharmacology 62:1182-1190 (2012).
Rutten et al., Rolipram reverses scopolamine-induced and time-dependent memory deficits in object recognition by different mechanisms of action., Neurobiology of Learning and Memory 85:132-138 (2006).
Rutten et al., Sub-chronic rolipram treatment leads to a persistent improvement in long-term object memory in rats, Neurobiology of Learning and Memory, 90:569-575 (2008).
Rutten et al., Phosphodiesterase Inhibitors Enhance Object Memory Independent of Cerebral Blood Flow and Glucose Utilization in Rats, Neuropsychopharmacology 34:1914-1925 (2009).
Rutten et al., Selective PDE inhibitors rolipram and sildenafil improve object retrieval performance in adult cynomolgus macaques, Psychopharmacology 196:643-648 (2008).
Van Duinen et al., PDE4(d) inhibition as a target for cognition enhancement: A translational approach, Abstract, Neuroscience Annual Meeting, vol. 42 (2012).
Wieschollleck et al., PDE4 inhibition enhances hippocampal synaptic plasticity in vivo and rescues MK801-induced impairment of long-term potentiation and object recognition memory in an animal model of psychosis, Transl Psychiatry, vol. 2 epub:1-11 (Mar. 2012).
Yeghiyan et al., Inhibition of phosphodiesterase-4 (PDE4) for treatment of cognitive deficits in schizophrenia: A single subject case study, Poster P-20-128, International J. Neuropsychopharmacology 13:246 (2010).
Zhang et al., Inhibition of Cyclic AMP Phosphodiesterase (PDE4) Reverses Memory Deficits Associated with NMDA Receptor Antagonism, Neuropsychopharmacology, 23(2):198-204 (2000).
Zhang et al., Effects of rolipram on scopolamine-induced impairment of working and reference memory in the radial-arm maze tests in rats, Psychopharmacology 150:311-316 (2000).
Excerpt EU Clinical Trial Register Roflumilast and Cognition, University Maastricht Study Oct. 17, 2012 (6 pages).
Clinical Trials.gov archive, Roflumilast and Cognition, University Maastricht Study Nov. 13, 2012 (3 pages).
Akkerman et al., "Object recognition testing: methodological considerations on exploration and discrimination measures," Behav. Brain Res., Jul. 2012, 232:335-347.
Albert et al., "The diagnosis of mild cognitive impairment due to Alzheimer's disease: Recommendations from the National Institute on Aging-Alzheimer's Association workgroups on diagnostic guidelines for Alzheimer's disease," Alzheimer's & Dementia, 2011, 7:270-279.
Ennaceur and Delaceur, "A new one-trial test for neurobiological studies of memory in rats. 1: Behavioral data," Behav. Brain Res, 1988, 31:47-59.
Frith, "Neuropsychology of schizophrenia: What are the implications of intellectual and experimental abnormalities for the neurobiology of schizophrenia?" Br. Med. Bull., 1996, 52:618-626.
Jolles et al., Maastricht Aging Study; determinants of cognitive aging; Maastricht, The Netherlands, Neuropsych Publishers, 1995.
Kessels et al., "Object Relocation: A program for setting up, running, and analyzing experiments on memory for object locations," Behav. Res. Methods Instrum. Comput., 1999, 31(3):423-428.
Mattson et al., "Modification of Brain Aging and Neurodegenerative Disorders by Genes, Diet, and Behavior," Physiol. Rev., 2000, 82:637-672.
Riedel et al., "Tryptophan depletion in normal volunteers produces selective impairment in memory consolidation," Psychopharmacology, 1999, 141(4):362-369.
Van der Elst et al., "Rey's verbal learning test: Normative data for 1855 healthy participants aged 24-81 years and the influence of age, sex, education, and mode of presentation," J. Int. Neuropsychol. Soc., 2005, 11(3):290-302.
USPTO Non-final Office Action issued in U.S. Appl. No. 14/460,579 dated Aug. 3, 2015, 21 pages.
G M. Rose, et al. "Phosphodiesterase Inhibitors for Cognitive Enhancement," Current Pharmaceutical Design, 2005, 11, 3329-3334.
Taiwan Search Report for Application No. 103128183, dated Mar. 9, 2018.

\* cited by examiner

TREATMENT OF COGNITIVE IMPAIRMENT WITH PDE4 INHIBITOR

CROSS-REFERENCE TO RELATED APPLICATIONS

This application claims priority to U.S. Application Ser. No. 61/866,643, filed Aug. 16, 2013, the contents of which are incorporated herein by reference in their entirety.

FIELD OF THE INVENTION

The present disclosure is directed to therapies for the treatment of cognitive impairment. More particularly, the present disclosure is directed to the treatment of cognitive impairment associated with aging, Alzheimer's disease or schizophrenia with a phosphodiesterase 4 inhibitor including roflumilast, a pharmaceutically acceptable salt of roflumilast, roflumilast-N-oxide and a pharmaceutically acceptable salt of roflumilast-N-oxide.

BACKGROUND OF THE INVENTION

Decline in cognitive function is a common occurrence in the aging population. Cognitive impairment has a negative impact on daily activities and quality of life. (Mattson MP et al; Physiol Rev Vol. 82, 2000, pp 637-672). The loss of cognitive function is pronounced and severe in patients suffering from pathological conditions such as Alzheimer's disease or other types of dementia. Further, prominent cognitive deficits are also present in depressed and schizophrenic patients (Blaney PH; Psychol Bull Vol 99, 1986, pp 229-246. Frith C; BR Med Bull, Vol 52, 1996, pp 618-626). Cognitive impairment has a significant impact on the quality of life of these patients. Hence, it is of critical importance that strategies and therapeutics to counteract cognitive decline are developed.

Phosphodiesterases have recently gained increased attention as potential new targets for cognition enhancement. Phosphodiesterases are enzymes that hydrolyze cyclic AMP (cAMP) and/or cyclic GMP (cGMP) in various cell types, including the brain. Evidence is accumulating that second messenger molecules, cGMP and cAMP, are important in memory processes in general and long-term potentiation in particular.

Prickaerts et al (Psychopharmacology Vol 202, 2009, pp 419-443) review the effects of different classes of selective phosphodiesterase inhibitors (inter alia phosphodiesterase 4 inhibitors) in in vivo murine models on cognition enhancement. International patent application WO01/87281 describes the use of a group of phosphodiesterase 4 inhibitors for enhancing cognitive function. Further, Bruno et al (Br J Pharmacol, Vol 164, 2011, pp 2054-2063) describe the effects of GEBR-7b, a PDE4D selective inhibitor, on the object recognition test on rats and mice. Additional studies have shown the effects of L-454,560 a selective phosphodiesterase 4 inhibitor, on the rat water maze Delayed Matching To Position (DMTP) test indicating possible cognitive (i.e., memory) enhancement effects of the compound (Huang Z et al, Biochem Pharmacol Vol 73, 2007, pp 1971-1981). Selective phosphodiesterase 4 inhibitor MK-0952 was tested in rats and showed an improvement of novel object recognition as well as in the Water Maze DMTP test in rats (Gallant M et al, Bioorganic and Medicinal Chemistry Letters 2010, Vol 20 (Issue 22), pp. 6387-6393).

Phosphodiesterase 4 inhibitors (PDE4 inhibitors) are known to produce dose-limiting adverse events, including emesis, nausea and colitis, rendering their clinical development challenging. Therefore, despite efforts through research to overcome these challenges and further due to the narrow therapeutic window of this class of phosphodiesterase 4 inhibitors, none of the tested phosphodiesterase 4 inhibitors has thus far shown (a) a sufficient efficacy in the clinic and at the same time also (b) an acceptable adverse event profile.

It is an object of the present invention to overcome this problem by using a known phosphodiesterase 4 inhibitor in a particular low dose for the treatment of cognitive impairment.

Definitions

As used herein, the term "treating cognitive impairment" or "treatment of cognitive impairment" refer to one or more of the following:

(1) inhibiting the disease and its progression; for example, inhibiting a disease, condition or disorder in an individual who is experiencing or displaying the pathology or sympathology of the disease, condition or disorder (i.e., arresting further development of the pathology and/or symptomatology) such as in case of cognitive impairment, arresting or delaying a) the decline in memory (long term and/or short term), b) the decline in decision making, c) the decline in executive functions (e.g., reasoning, problem-solving, planning), d) the decline in language skills (e.g., naming, fluency, expressive speech, and comprehension), e) the decline in visuospatial skills, and f) the decline in attentional control (e.g., simple and divided attention), (2) ameliorating the disease; for example, ameliorating a disease, condition or disorder in an individual who is experiencing or displaying the pathology or symptomatology of the disease, condition or disorder (i.e., reversing the pathology or symptomatology) such as in case of cognitive impairment, a) improvement in memory (long term and/or short term), b) improvement in decision making, c) improvement in executive functions (e.g., reasoning, problem-solving, planning), d) improvement in language skills (e.g., naming, fluency, expressive speech, and comprehension), e) improvement in visuospatial skills, and f) improvement in attentional control (e.g., simple and divided attention).

As used herein, the term "mammal" has its ordinary meaning in the art and includes, e.g. humans, mice, rats, rabbits, dogs, cats, bovines, horses, swine and monkey, with preference given to humans.

As used herein, the phrase "cognitive impairment" refers to any decline in one or more of memory functions, decision making, executive functions, language skills, visuospatial skills, or attentional control.

Cognitive impairment may be associated with aging as well as with a variety of disorders. Disorders, which may be mentioned in this connection are, for example, Mild Cognitive Impairment (MCI) associated with Alzheimer's disease, cognitive impairment associated with Alzheimer's disease, cognitive impairment associated with Schizophrenia (CIAS), cognitive impairment associated with Vascular disease, cognitive impairment associated with Parkinson's disease, cognitive impairment associated with Huntington's disease, cognitive impairment due to stroke, cognitive impairment due to attention deficit disorder, cognitive impairment due to depression, frontotemporal dementia due to motor neuron disease and post-operative cognitive decline (POCD) in the elderly.

Sharp demarcations between normal cognition and mild cognitive impairment and between mild cognitive impairment and cognitive impairment associated with Alzheimer's Disease are difficult. Clinical judgment must be used to make these distinctions. As used herein, the phrase "mild cognitive impairment" refers to the symptomatic predementia phase of Alzheimer's disease. Criteria that should be met in order to diagnose a person with "mild cognitive impairment" include the following (Albert M S et al; Alzheimer's & Dementia 2011 Vol 7, pp 270-279):

- there should be evidence of concern about a change in cognition, in comparison with the person's previous level
- there should be evidence of lower performance in one or more cognitive domains that is greater than expected for the patient's age, and educational background; this lower performance can occur in a variety of cognitive domains, including memory, executive function, attention, language, and visuospatial skills
- Persons with mild cognitive impairment commonly have mild problems performing complex functional tasks which they used to perform previously, such as paying bills, preparing a meal, or shopping; they may take more time, be less efficient, and make more errors at performing such activities than in the past
- The cognitive changes are sufficiently mild that there is no evidence of a significant impairment in social or occupational life
- Scores on cognitive tests for individuals with mild cognitive impairment are typically 1 to 1.5 standard deviations below the mean for their age and education matched peers on culturally appropriate normative data (i.e., for the impaired domain(s)); age and educational norms are available for some tests, as for example Verbal Learning Tests such as California Verbal Learning Test (CVLT) or Fre and Cued Selective Reminding Test (FCSRT).

In general, "pharmaceutically acceptable salts" refers to salts with inorganic bases, salts with organic bases, salts with inorganic acids, salts with organic acids, and salts with basic or acidic amino acids.

Examples of salts with inorganic bases may include salts with alkali metals such as sodium, potassium, etc., salts with alkaline earth metals such as calcium, magnesium, etc., and salts with aluminum etc.

Examples of salts with organic bases may include salts with trimethylamine, triethylamine, pyridine, picoline, ethanolamine, diethanolamine, triethanolamine, dicyclohexylamine, N,N-dibenzylethylenediamine, etc.

Examples of salts with inorganic acids may include salts with hydrochloric acid, hydrobromic acid, nitric acid, sulfuric acid, phosphoric acid, etc.

Examples of salts with organic acids may include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Examples of salts with basic amino acids may include salts with arginine, lysine, ornithine, etc.; examples of salts with acidic amino acids may include salts with aspartic acid, glutamic acid, etc.

"Unit dosage forms", as used herein, refers to physically discrete units suitable as unitary dosages for human subjects and other mammals, each unit containing a predetermined quantity of active material calculated to produce the desired therapeutic effect, in association with a suitable pharmaceutical excipient.

SUMMARY OF THE INVENTION

In one embodiment, the present invention provides a method of treating cognitive impairment in a mammal in need of such treatment, including administering to a mammal suffering from cognitive impairment a phosphodiesterase 4 inhibitor. The PDE4 inhibitor may be selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor may be administered at a daily dose of between 50 and 300 mcg or preferably at a daily dose of 50 to 150 mcg.

In another embodiment, the present invention provides a method of treating mild cognitive impairment in a mammal in need of such treatment, including administering to a mammal suffering from mild cognitive impairment a phosphodiesterase 4 inhibitor. The PDE4 inhibitor may be selected from the group consisting of roflumilast, a pharmaceutically acceptable salt of roflumilast, roflumilast-N-oxide and a pharmaceutically acceptable salt of roflumilast-N-oxide. The phosphodiesterase 4 inhibitor may be administered at a daily dose of between 50 and 300 mcg or preferably at a daily dose of between 50 and 150 mcg.

In another embodiment, the present invention provides a method of treating cognitive impairment associated with Alzheimer's disease, schizophrenia or aging in a mammal in need of such treatment, including administering to a mammal suffering from cognitive impairment associated with Alzheimer's disease, schizophrenia or aging, a phosphodiesterase 4 inhibitor. The PDE4 inhibitor may be selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor may be administered at a daily dose of between 50 and 300 mcg.

DETAILED DESCRIPTION OF THE INVENTION

Figure 1:
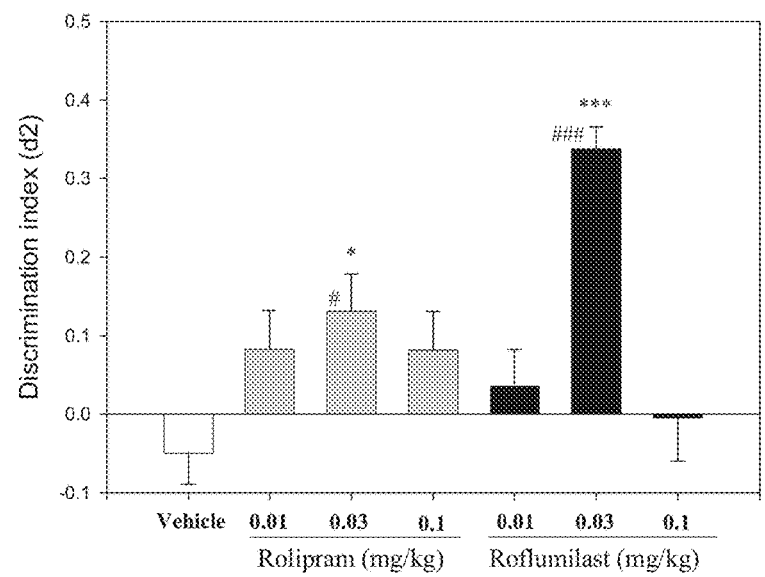
FIG. 1 depicts the dose response effects of rolipram and of roflumilast on the discrimination index in the object location task test following a 24-hour retention interval in mice.

The present invention provides a method of treating cognitive impairment. More particularly, the present invention provides a method of treating cognitive impairment associated with aging, Alzheimer's disease or schizophrenia comprising administering to a mammal in need of such treatment a phosphodiesterase 4 inhibitor at a specified low dose. Moreover, the present invention may be used to delay the progress of mild cognitive impairment into severe cognitive impairment.

Roflumilast is the only phosphodiesterase 4 inhibitor that has been approved so far for the treatment of severe Chronic Obstructive Pulmonary Disease (COPD). The US label mentions that roflumilast is indicated as a treatment to reduce the risk of COPD exacerbations in patients with severe COPD associated with chronic bronchitis and a history of exacerbations. The recommended dosage for patients with COPD is one 500 microgram (mcg) tablet per day.

The administration of a PDE4 inhibitor selected from the group including roflumilast, a pharmaceutically acceptable salt of roflumilast, roflumilast-N-oxide and a pharmaceutically acceptable salt of roflumilast-N-oxide is described for the treatment of cognitive impairment whereby the effects of the treatment can be evaluated, for example, by one or more of the following: arresting or delaying the decline, or providing improvement in:

a) memory (long term and/or short term),
b) decision making,
c) executive functions (e.g., reasoning, problem-solving, planning),
d) language skills (e.g., naming, fluency, expressive speech, and comprehension),
e) visuospatial skills, and
f) attentional control (e.g., simple and divided attention)

A major metabolite of roflumilast in humans and several animal species is roflumilast-N-oxide, which is by itself a potent phosphodiesterase 4 inhibitor. It is believed that roflumilast-N-oxide accounts for more than 90% of overall phosphodiesterase 4 inhibition in humans and that therefore, roflumilast-N-oxide largely governs the pharmacological effects observed in humans after the administration of roflumilast.

Mouse studies have shown a pronounced effect on spatial memory measured by the object location task test following a single subcutaneous administration of 0.03 mg/kg roflumilast, while nearly no effect was detected after a single subcutaneous administration of 0.01 mg/kg roflumilast and completely no effect was noted following a single subcutaneous administration of 0.1 mg/kg roflumilast.

Based on the results obtained in the object location task test in mice, a clinical trial involving healthy 18 to 35 year old adults was performed using a single oral administration of a capsulated formulation containing 100 mcg, 300 mcg or 1000 mcg roflumilast.

In this clinical trial the group of healthy adults receiving a single oral dose of 100 mcg of roflumilast showed a considerable improvement with respect to the number of correct words recalled (an average 2.5 words improvement after the third trial) in the verbal learning task (VLT). EEG measurements performed simultaneously with VLT testing revealed that Event-Related Potential (ERP), P600 demonstrated the strongest increase of amplitude, also in the group of healthy adults receiving a single oral dose of 100 mcg of roflumilast.

In the above-indicated clinical trial roflumilast was administered once in a single oral dose of 100 mcg, 300 mcg or 1000 mcg. Due to the pharmacokinetics of roflumilast and its metabolite roflumilast-N-oxide and the median plasma half-life of these compounds the steady state plasma concentration levels in a once a day (24 h) repeated dosing regimen of roflumilast/roflumilast-N-oxide is about two-fold compared to the plasma concentration levels following a once a day single dosing. Thus the administration of a single oral dose of 100 mcg, 300 mcg or 1000 mcg roflumilast leads to comparable plasma concentration levels as 50 mcg, 150 mcg and 500 mcg roflumilast in the steady state once a day (24 h) repeated dosing regimen.

In rat studies the data obtained in the mouse studies have been confirmed. A single intraperitoneally administered dose of 0.003 mg/kg roflumilast was able to fully restore spatial memory function (measured by the object recognition task) in rats treated with scopolamine to induce memory deficit. Single intraperitoneally administered doses of 0.01 mg/kg, 0.03 mg/kg, 0.001 mg/kg and 0.0003 mg/kg roflumilast showed increasingly less efficacy on restoring spatial memory function. No effect was noted following a single intraperitoneally administration of 0.0001 mg/kg roflumilast.

In order (a) to confirm the results seen in the clinical trial with the healthy 18 to 35 years old adults and (b) to detect whether perhaps even more substantial improvement might be observed in aged adults with a certain degree of cognitive impairment, a clinical study is conducted with forty 60 to 80 year old subjects with one group having a more pronounced cognitive decline (impaired group: 1 to 2 standard deviations below the mean for their age and education matched peers on culturally appropriate normative data assessed with Verbal Learning Test) as well as with an aged matched control group (control group: −0.5-+0.5 standard deviations below and above the mean for their age and education matched peers on culturally appropriate normative data assessed with Verbal Learning Test). The two patients groups are tested for cognitive battery (Verbal Learning Task, Spatial Memory Task and Stroop Task) and EEG battery (ERP's, sensory gating and novelty oddball task) tests. The data obtained from an interim analysis of that clinical trial based on 9 subjects of the impaired group and 4 subjects of the control group appears to confirm the effects seen in the Verbal Learning Task in the earlier trial with healthy adults after administration of 100 mcg of roflumilast.

All these data indicate that roflumilast administered in doses considerably lower than the approved once a day dose for the treatment of severe COPD (500 mcg), is effective in improving cognitive impairment.

In a first aspect, the present invention therefore is directed to a method of treating cognitive impairment in a mammal in need of such treatment, comprising administering to a mammal suffering from cognitive impairment a phosphodiesterase 4 inhibitor selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor is administered at a daily dose of between 50 and 300 mcg.

Cognitive impairment may be associated with aging as well as with a variety of disorders. Disorders, which may be mentioned in this connection are, for example, Mild Cognitive Impairment (MCI) associated with Alzheimer's disease, cognitive impairment associated with Alzheimer's disease, cognitive impairment associated with Schizophrenia (CIAS), cognitive impairment associated with Vascular disease, cognitive impairment associated with Parkinson's disease, cognitive impairment associated with Huntington's disease, cognitive impairment due to stroke, cognitive impairment due to attention deficit disorder, cognitive impairment due to depression, frontotemporal dementia due to motor neuron disease and post-operative cognitive decline (POCD) in the elderly.

In a second aspect the present invention therefore is directed to a method of treating mild cognitive impairment in a mammal in need of such treatment, comprising administering to a mammal suffering from mild cognitive impairment a phosphodiesterase 4 inhibitor selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor is administered at a daily dose of between 50 and 300 mcg.

In a third aspect, the present invention therefore is directed to a method of treating cognitive impairment associated with Alzheimer's disease, schizophrenia or aging in a mammal in need of such treatment, comprising administering to a mammal suffering from cognitive impairment associated with Alzheimer's disease, schizophrenia or aging, a phosphodiesterase 4 inhibitor selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor is administered at a daily dose of between 50 and 300 mcg.

In one embodiment of the third aspect of the invention, the cognitive impairment is associated with Alzheimer's disease.

In a further embodiment of the third aspect of the invention, the cognitive impairment is associated with schizophrenia.

In a further embodiment of the third aspect of the invention, the cognitive impairment is associated with aging.

In a preferred embodiment of the first, second and third aspect of the invention, the phosphodiesterase 4 inhibitor is selected from the group consisting of roflumilast and a pharmaceutically acceptable salt of roflumilast.

In another preferred embodiment of the first, second and third aspect of the invention, the phosphodiesterase 4 inhibitor is selected from the group consisting of roflumilast-N-oxide and a pharmaceutically acceptable salt of roflumilast-N-oxide.

In a particularly preferred embodiment of the first, second and third aspect of the invention, the phosphodiesterase 4 inhibitor is roflumilast.

In another particularly preferred embodiment of the first, second and third aspect of the invention, the phosphodiesterase 4 inhibitor is roflumilast-N-oxide.

Patients suffering from cognitive impairment associated with Alzheimer's disease or schizophrenia may already receive medication intended to treat the cognitive impairment feature/aspect of Alzheimer's disease or schizophrenia or other feature(s)/aspect(s) of Alzheimer's disease or schizophrenia.

In a fourth aspect, the present invention therefore is directed to a method of treating cognitive impairment associated with Alzheimer's disease in a mammal in need of such treatment comprising administering to a mammal suffering from cognitive impairment associated with Alzheimer's disease, who already receives medication for Alzheimer's disease treatment, as a supplement to the medication for Alzheimer's disease treatment, a phosphodiesterase 4 inhibitor selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor is administered at a daily dose of between 50 and 300 mcg.

In an embodiment of the fourth aspect, the mammal suffering from cognitive impairment associated with Alzheimer's disease receives already a medication selected from the group consisting of donepezil, rivastigmine, galantamine, memantine and a pharmaceutically acceptable salt of these compounds.

In a preferred embodiment of the fourth aspect, the mammal suffering from cognitive impairment associated with Alzheimer's disease already receives donepezil hydrochloride for Alzheimer's disease treatment.

In a fifth aspect, the present invention therefore is directed to a method of treating cognitive impairment associated with schizophrenia in a mammal in need of such treatment comprising administering to a mammal suffering from cognitive impairment associated with schizophrenia, who already receives medication for schizophrenia treatment, as a supplement to the medication for schizophrenia treatment, a phosphodiesterase 4 inhibitor selected from the group consisting of roflumilast, a pharmaceutically acceptable salt of roflumilast, roflumilast-N-oxide and a pharmaceutically acceptable salt of roflumilast-N-oxide, wherein the phosphodiesterase 4 inhibitor is administered at a daily dose of between 50 and 300 mcg.

In an embodiment of the fifth aspect, the mammal suffering from cognitive impairment associated with Schizophrenia already receives a medication for schizophrenia treatment selected from first and second generation antipsychotics, such as, but not limited to, chlorpromazine, haloperidol, perphenazine, fluphenazine, aripiprazole and a pharmaceutically acceptable salt of these compounds.

Roflumilast, the pharmaceutically acceptable salt of roflumilast, roflumilast-N-oxide or the pharmaceutically acceptable salt of roflumilast-N-oxide may be administered to the patient in need of treatment once daily, twice daily, three or four times a day. Once daily administration is particularly preferred. Treatment should be preferably administered at the same time each day.

In the present invention, roflumilast or roflumilast-N-oxide, in terms of their free form may be administered at a daily dose of about 50 mcg to about 300 mcg, such as 50, 62.5, 75, 100, 125, 150, 175, 200, 250 or 300 mcg, preferably at the dose of 50, 62.5, 75, 100, 125 or 150 mcg, more preferably at a dose of 50, 75, 100 or 125 mcg.

If a twice daily administration is intended instead of a once daily administration, the above indicated amounts of roflumilast or roflumilast-N-oxide can be divided in half.

Corresponding amounts of a pharmaceutically acceptable salt of roflumilast (roflumilast-N-oxide) can easily be calculated, depending on the choice of the respective salt.

In one embodiment of the first, second, third, fourth and fifth aspect of the invention, the phosphodiesterase 4 inhibitor is administered at a daily dose of 300 mcg.

In a further embodiment of the first, second, third, fourth and fifth aspect of the invention, the phosphodiesterase 4 inhibitor is roflumilast and is administered at a daily dose of 300 mcg.

In another embodiment of the first, second, third, fourth and fifth aspect of the invention, the phosphodiesterase 4 inhibitor is administered at a daily dose of 250 mcg.

In another embodiment of the first, second, third, fourth and fifth aspect of the invention, the phosphodiesterase 4 inhibitor is roflumilast and is administered at a daily dose of 250 mcg.

In another embodiment of the first, second, third, fourth and fifth aspect of the invention, the phosphodiesterase 4 inhibitor is administered at a daily dose of 200 mcg.

In another embodiment of the first, second, third, fourth and fifth aspect of the invention, the phosphodiesterase 4 inhibitor is roflumilast and is administered at a daily dose of 200 mcg.

In another embodiment of the first, second, third, fourth and fifth aspect of the invention, the phosphodiesterase 4 inhibitor is administered at a daily dose of 175 mcg.

In another embodiment of the first, second, third, fourth and fifth aspect of the invention, the phosphodiesterase 4 inhibitor is roflumilast and is administered at a daily dose of 175 mcg.

In a preferred embodiment of the first, second, third, fourth and fifth aspect of the invention, the phosphodiesterase 4 inhibitor is administered at a daily dose of between 50 and 150 mcg.

In a particularly preferred embodiment of the first, second, third, fourth and fifth aspect of the invention, the phosphodiesterase 4 inhibitor is roflumilast and is administered at a daily dose of between 50 and 150 mcg.

In another preferred embodiment of the first, second, third, fourth and fifth aspect of the invention, the phosphodiesterase 4 inhibitor is administered at a daily dose of 150 mcg.

In another particularly preferred embodiment of the first, second, third, fourth and fifth aspect of the invention, the phosphodiesterase 4 inhibitor is roflumilast and is administered at a daily dose of 150 mcg.

In another preferred embodiment of the first, second, third, fourth and fifth aspect of the invention, the phosphodiesterase 4 inhibitor is administered at a daily dose of 125 mcg.

In another particularly preferred embodiment of the first, second, third, fourth and fifth aspect of the invention, the phosphodiesterase 4 inhibitor is roflumilast and is administered at a daily dose of 125 mcg.

In another preferred embodiment of the first, second, third, fourth and fifth aspect of the invention, the phosphodiesterase 4 inhibitor is administered at a daily dose of 100 mcg.

In another particularly preferred embodiment of the first, second, third, fourth and fifth aspect of the invention, the phosphodiesterase 4 inhibitor is roflumilast and is administered at a daily dose of 100 mcg.

In another preferred embodiment of the first, second, third, fourth and fifth aspect of the invention, the phosphodiesterase 4 inhibitor is administered at a daily dose of 75 mcg.

In another particularly preferred embodiment of the first, second, third, fourth and fifth aspect of the invention, the phosphodiesterase 4 inhibitor is roflumilast and is administered at a daily dose of 75 mcg.

In another preferred embodiment of the first, second, third, fourth and fifth aspect of the invention, the phosphodiesterase 4 inhibitor is administered at a daily dose of 62.5 mcg.

In another particularly preferred embodiment of the first, second, third, fourth and fifth aspect of the invention, the phosphodiesterase 4 inhibitor is roflumilast and is administered at a daily dose of 62.5 mcg.

In another preferred embodiment of the first, second, third, fourth and fifth aspect of the invention, the phosphodiesterase 4 inhibitor is administered at a daily dose of 50 mcg.

In another particularly preferred embodiment of the first, second, third, fourth and fifth aspect of the invention, the phosphodiesterase 4 inhibitor is roflumilast and is administered at a daily dose of 50 mcg.

Roflumilast

The chemical name of roflumilast is N-(3,5-dichloropyridin-4-yl)-3-cyclopropylmethoxy-4-difluoromethoxybenzamide [or alternatively: 3-cyclopropylmethoxy-4-difluoromethoxy N-(3,5-dichloropyridin-4-yl) benzamide].

The structural formula of roflumilast is:

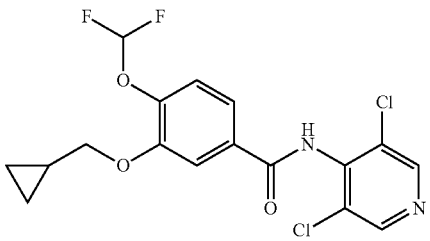 [SMILES: O=C(Nc1c(Cl)cncc1Cl)c1ccc(OC(F)F)c(OCC2CC2)c1]

The phosphodiesterase 4 inhibitor roflumilast is disclosed in U.S. Pat. No. 5,712,298 (hereby incorporated by reference in its entirety).

Pharmaceutically acceptable salts of roflumilast include the sodium and the potassium salt of roflumilast. Roflumilast is preferably used in its free form rather than in the form of a pharmaceutically acceptable salt thereof.

The chemical name of roflumilast-N-oxide is 3-cyclopropyl-methoxy-4-difluoromethoxy-N-(3,5-dichloro-1-oxy-pyrid-4-yl)benzamide. Roflumilast-N-oxide (also referred to as the pyridyl N-oxide of roflumilast), is the major active metabolite of roflumilast in humans, and is itself a potent phosphodiesterase 4 inhibitor.

Pharmaceutically acceptable salts of roflumilast-N-oxide may include the sodium and the potassium salt of roflumilast-N-oxide. Roflumilast-N-oxide is preferably used in its free form rather than in the form of a pharmaceutically acceptable salt thereof.

Roflumilast may be synthesized as disclosed in U.S. Pat. Nos. 5,712,298 and 7,470,791. Each of these U.S. patents is hereby incorporated by reference in its entirety.

Roflumilast may be formulated in a variety of dosage forms for administration by several routes of administration. Roflumilast tablets may be prepared as disclosed in U.S. Pat. No. 7,951,397, which is hereby incorporated by reference in its entirety. Taste masking formulations for oral dosage forms are disclosed in WO2006/097456 (U.S. patent application No. 2008-0193544) which is hereby incorporated by reference in its entirety.

Transdermal dosage forms for roflumilast are disclosed in WO2003/099334 (U.S. patent application No. 2006-0084684 which is hereby incorporated by reference in its entirety) as are other formulations for topical administration, e.g., creams, ointments, gels and pastes. Preparations of roflumilast solutions for injection are disclosed in WO2006/032675 (U.S. patent application No. 2007-0259009 which is hereby incorporated by reference in its entirety).

Pharmaceutical Formulations and Dosage Forms

When employed as a pharmaceutical, roflumilast, the pharmaceutically acceptable salt of roflumilast, roflumilast-N-oxide or the pharmaceutically acceptable salt of roflumilast-N-oxide (hereinafter collectively referred to as "the compounds of the invention") can be administered in the form of pharmaceutical composition(s). These pharmaceutical composition(s) can be prepared in a manner well known in the pharmaceutical art and can be administered by a variety of routes.

Administration can be pulmonary (e.g., by inhalation or insufflation of powders or aerosols, including by nebulizer, intratracheal, intranasal, epidermal and transdermal), oral or parenteral. Parenteral administration includes intravenous, subcutaneous, intraperitoneal or intramuscular injection, or infusion. Parenteral administration can be in the form of a single bolus dose or for example, can be by a continuous perfusion pump. Pharmaceutical composition(s) and formulations for topical administration can include: transdermal patches; conventional pharmaceutical carriers; aqueous, powder or oily bases; thickeners; and/or the like which may be necessary or desirable. Oral administration is particularly preferred.

This invention also includes pharmaceutical composition(s) which contain, as the active ingredient, one or more of the compounds of the invention in combination with one or more pharmaceutically acceptable carriers. Pharmaceutically acceptable carriers known in the art can be employed. In making the pharmaceutical composition(s) of the invention, the active ingredients are typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the pharmaceutical composition(s) can be in the form of tablets, pills, powders, lozenges, sachets, cachets, elixirs, suspensions, emulsions, solutions, syrups, aerosols (as a solid or in a liquid medium), soft and hard gelatin capsules, suppositories, sterile injectable solutions, and sterile packaged powders. Solid pharmaceutical compositions in the form of tablets for oral administration are particularly preferred.

The pharmaceutical composition(s) can be formulated in a unit dosage form, each dosage containing an amount of the active ingredient as described above.

Examples Of Roflumilast Tablet Formulations:

Example A: 250 mcg Roflumilast

| | |
|---|---|
| Roflumilast | 0.250 mg |
| Lactose monohydrate | 49.660 mg |
| Corn starch | 13.390 mg |
| Polyvidone K90 | 1.300 mg |
| Magnesium stearate | 0.650 mg |

Example B: 125 mcg Roflumilast

| | |
|---|---|
| Roflumilast | 0.125 mg |
| Lactose monohydrate | 49.660 mg |
| Corn starch | 13.390 mg |
| Polyvidone K90 | 1.300 mg |
| Magnesium stearate | 0.650 mg |

Example C: 100 mcg Roflumilast

| | |
|---|---|
| Roflumilast | 0.100 mg |
| Lactose monohydrate | 49.660 mg |
| Corn starch | 13.390 mg |
| Polyvidone K90 | 1.300 mg |
| Magnesium stearate | 0.650 mg |

Example D: 75 mcg Roflumilast

| | |
|---|---|
| Roflumilast | 0.075 mg |
| Lactose monohydrate | 49.660 mg |
| Corn starch | 13.390 mg |
| Polyvidone K90 | 1.300 mg |
| Magnesium stearate | 0.650 mg |

Example E: 50 mcg Roflumilast

| | |
|---|---|
| Roflumilast | 0.050 mg |
| Lactose monohydrate | 49.660 mg |
| Corn starch | 13.390 mg |
| Polyvidone K90 | 1.300 mg |
| Magnesium stearate | 0.650 mg |

EXAMPLES

The specific examples below are to be construed as merely illustrative, and not limitative of the remainder of the disclosure in any way whatsoever. Without further elaboration, it is believed that one skilled in the art can, based on the description herein, utilize the present invention to its fullest extent.

Example 1

Analysis of Cognitive Improvement Effects of Roflumilast on Spatial Memory in Mice The objective of this study was to evaluate the cognitive improvement effects of Roflumilast on spatial memory employing Object Location Task (OLT) in male C57BL/6NCrl mice. Roflumilast was compared with data of the already established PDE4 inhibitor Rolipram in the same model.

Methods

Maintenance of Animals Twenty-four 7 month-old male C57BL/6NCrl mice (Charles River, L'Arbresle, France) were used (average body weights: 27.6 g). The animals were kept under a 12/12-hour light/dark cycle (lights on from 07.00 pm to 07.00 am) with free access to food and water. All testing was done between 09.00 am and maximally 06.00 pm.

Preparation of Compounds for Administration Both rolipram (Sigma-Aldrich St. Louis, USA; MW 275.34) and roflumilast (Biocrea, Radebeul, Germany; MW 403.21) were dissolved in dimethylsulfoxide (DMSO) and kept at 4° C.; this stock solution was used for further dilutions in 0.5% methylcellulose. Each of rolipram and roflumilast is used in form of its free base. All injected solutions consisted of 0.5% methylcellulose with a fixed DMSO percentages (1.2%) (vehicle).

Object Location Task Studies in Rodents For the Object Location Task (OLT), doses of 0.01 mg/kg, 0.03 mg/kg and 0.1 mg/kg of Rolipram or Roflumilast or vehicle were administered subcutaneously (s.c.). Based on previous findings, PDE4 inhibitor single administration was performed 3 hours after the first trial as this has an optimum effect on object memory performance. The injection volume was 5 µl/g.

The OLT apparatus consisted of a circular arena, 40 cm in diameter. Half of the 40 cm transparent polyvinyl chloride wall was covered from the outside with white paper. Two objects were placed symmetrically about 10 cm away from the wall on the separation line, between the transparent and covered side of the arena. Four different sets of objects were available: (1) a cone made of brass (maximal diameter 6 cm and total height 3.8 cm), (2) a transparent glass bottle (diameter 2.7 cm, height 8.5 cm) filled with sand and water, (3) a massive metal cube (2.5 cm×5 cm×7.5 cm) with two holes (diameter 1.5 cm), and (4) a massive aluminum cube with a tapering top (4.5 cm×4.5 cm×8.5 cm).

A testing session comprised two trials of 4 minutes. Before each trial, mice were placed in an empty Makrolon cage (incubation cage) for the same amount of time as the trial (4 min). During the first trial (T1), two identical objects were placed symmetrically about 10 cm away from the wall on the separation line between the transparent and covered side of the arena. After the first exploration period of 4 min, the mouse was put back in its home cage. Mice then received treatment at 3 hours post T1. Subsequently, after a predetermined delay interval (24h), the mouse was placed in the apparatus for the second trial of 4 min (T2). Two identical objects as in T1 were used; one object was placed in the previously used position, whereas the other was placed in a novel position. The novel position of the object could either be a fixed distance towards the front or a fixed distance towards the back of the arena for both objects. The times spent exploring each object during T1 and T2 were recorded manually using a personal computer. All objects and locations were used in a balanced manner to exclude possible object and/or location preferences. To avoid olfactory cues, the objects were thoroughly cleaned with 70% ethanol after each trial. The testing order of conditions was determined randomly.

Statistical Data Analysis The measurements reflected the time spent by the mice in exploring each object during T1 and T2. The time spent in exploring the two identical samples in T1 were represented by 'a1' and 'a2', respectively. The time spent in exploring the sample and the new object in T2 were represented by 'a' and 'b', respectively. From these exploration times the following variables were calculated: e1, e2, and d2 (Table 1). The d2 index is a relative measure of discrimination corrected for exploratory activity. The d2 index can range from −1 to 1, with −1 or 1 indicating complete preference for the familiar or novel object, respectively, and 0 signifying no preference for either object.

TABLE 1

Derived Measures in the OLT

| Trial number | Exploration time (sec) | Discrimination index |
|---|---|---|
| T1 | e1 = a1 + a2 | — |
| T2 | e2 = a + b | d2 = (b − a)/e2 |

One-sample t-statistics were performed in order to assess whether the d2 index for each treatment group differed significantly from zero. However, comparison of the value of d2 with the value zero with no variance may not be the most suitable way of analyzing object recognition since there was an increased chance of making a type I error. Treatment groups were therefore also compared using one-way ANOVAs. When the overall ANOVA was significant, a post-hoc analysis with Bonferroni t-tests (all pairwise comparisons) was performed. An $\alpha$ level of 0.05 was considered significant.

Results

The results of the exploration times (e1 and e2) and the discrimination measures (d2) for each of the different groups are summarized in Table 2. There were no differences in exploration time between treatment conditions for both T1 (e1: $F(6,113)=1.27$, n.s.) and T2 (e2: $F(6,113)=1.66$, n.s.). One mouse was excluded from the analysis in the rolipram 0.1 mg/kg and roflumilast 0.01 mg/kg condition due to insufficient exploration times (<7.5 seconds). Number of animals used in the study was: vehicle 23; rolipram 0.01 mg/kg: 16; rolipram 0.03 mg/kg: 16; rolipram 0.1 mg/kg: 15; roflumilast 0.01 mg/kg: 15; roflumilast 0.03 mg/kg: 16; roflumilast 0.1 mg/kg: 16.

TABLE 2

Means (±SEM) for the Derived Measures in the OLT

A: Rolipram

| Group number | Dose level Rolipram (mg/kg, s.c.) | e1 (s) | e2 (s) | d2 index |
|---|---|---|---|---|
| 1 | Vehicle | 13.87 (0.73) | 13.36 (0.71) | −0.05 (−0.04) |
| 2 | 0.01 | 15.58 (0.95) | 12.99 (0.84) | 0.08 (0.05) |
| 3 | 0.03 | 15.45 (1.35) | 13.56 (0.95) | 0.13 (0.05) # |
| 4 | 0.1 | 15.82 (1.03) | 12.29 (0.08) | 0.07 (0.05) | e1, total exploration time during T1
e2, total exploration time during T2
d2 index, discrimination index between the new and familiar objects for T2
The d2 index differed from zero by one-sample t-tests: #: $p < 0.05$.

B: Roflumilast

| Group number | Dose level Roflumilast (mg/kg, s.c.) | e1 (s) | e2 (s) | d2 index |
|---|---|---|---|---|
| 1 | Vehicle | 13.87 (0.73) | 13.36 (0.71) | −0.05 (−0.04) |
| 2 | 0.01 | 15.95 (1.11) | 14.13 (1.22) | 0.04 (0.05) |
| 3 | 0.03 | 15.62 (1.37) | 16.13 (1.18) | 0.34 (0.03) ### |
| 4 | 0.1 | 17.51 (1.36) | 13.73 (1.11) | 0.00 (0.06) | e1, total exploration time during T1
e2, total exploration time during T2
d2 index, discrimination index between the new and familiar objects for T2
The d2 index differed from zero by one-sample t-tests: ###: $p < 0.001$.

One-sample t-tests showed that the d2 indices of the rolipram 0.03 mg/kg and roflumilast 0.03 mg/kg conditions significantly differed from zero, indicating that mice discriminated between locations after twenty-four hours (Table 2 and FIG. 1). Between group comparisons showed significant differences between rolipram conditions ($F(3,68)=3.99$, $p<0.05$). Post-hoc analysis revealed that the d2 index in the rolipram 0.03 mg/kg condition differed significantly from the vehicle condition (FIG. 1). Between group comparisons of the roflumilast conditions also showed significant differences ($F(3,68)=15.71$, $p<0.001$). Post-hoc analysis revealed that the d2 index of the roflumilast 0.03 mg/kg condition differed significantly from the vehicle condition (FIG. 1).

In the OLT, roflumilast and rolipram were effective at the same dose of 0.03 mg/kg in improving spatial memory. Interestingly, the discrimination index (d2) for the Roflumilast treatment had a higher absolute value compared with the rolipram treatment, indicating that Roflumilast may have a stronger impact on spatial memory performance.

As shown in FIG. 1, when compared with vehicle treatment, both rolipram and roflumilast 0.03 mg/kg conditions had a significantly higher d2 index. In FIG. 1, a significant difference from the vehicle condition is depicted with asterisks (Bonferroni comparison t-test: *: $p<0.05$, ***: $p<0.001$). A difference from zero is depicted with hashes (one-sample t-tests: #: $p<0.05$, ###: $p<0.001$).

Since emesis is a typical side-effect of phosphodiesterase 4 inhibitors the emetic potential of roflumilast and rolipram was investigated in parallel using the xylazine/ketamine induced α2-adrenergic receptor-mediated anesthesia test. The results confirmed that the two phosphodiesterase 4 inhibitors have different effects on emesis. Rolipram showed a strong emetic potential already with a dose of 0.3 mg/kg. In contrast, roflumilast only showed a tendency towards emetic potential at a dose of 3.0 mg/kg.

The present data show that roflumilast is a better alternative for memory enhancement than rolipram since its effect on memory is more potent while its emetic potential is much lower (i.e., wider therapeutic window in human) than that of rolipram.

Example 2

Analysis of Effects of Roflumilast on Cognition in Healthy Adults

The objective of this proof-of-concept study was to validate Roflumilast as cognitive enhancer using a translational behavior (i.e., cognitive testing)—EEG (i.e., brain electrical activity) approach. The study was intended to demonstrate whether memory, as well as attention, information processing, and executive function improved upon administration of Roflumilast in healthy adults.

This single center, randomized, double blind, efficacy study had a four-period crossover design and used single administration in healthy adults (n=20; 18 to 35 years; both males and females) of Roflumilast (capsulated formulation of 100 mcg, 300 mcg, and 1000 mcg) and of placebo with each period being ten to twenty-one days apart.

Method

Verbal Learning Task Analysis_The study utilized Verbal Learning Task (VLT) to analyze the increased number of words remembered following roflumilast administration. The VLT consisted of displaying 30 monosyllable words on a computer screen for a period of 60 seconds. Immediately after the presentation of the words on the computer screen subjects were asked to report as many words as they could recall by memory. This process (presentation and recall) was repeated further two times. In addition, 45 min and 24 h after the last presentation, subjects were again asked to report as many words as they could recall by memory. The set of three recall trials was conducted 60 minutes following administration of the roflumilast therapy.

Event Related Potential Analysis An electroencephalogram (EEG) cap was used to place a set of 32 EEG electrodes according to the international 10-20 system on the subjects. Event Related Potentials (ERPs) were extracted by averaging the responses within an epoch of 100 ms before and 1000 ms after stimulus onset covering P300, N400, and P600. Separate averages were made for correct and incorrect responses within a task and for different trial types. EEG measurements were done simultaneously with VLT testing. ERPs were calculated from the words that were called during immediate recall (encoding), and from the words that were recognized and from those that were not during the recognition condition at 45 minutes. The ERP components of P300, N400, and P600 were compared to examine whether the initial stimulus processing during the learning trials differs from word to word. Finally, ERPs to the old and new items during the recognition task were measured.

In addition to the VLT (immediate recall and delayed recall), the subjects were also tested in the Spatial Memory Task, the Stroop task and the Continuous Performance task (a description of these additional cognitive battery tests can be found in Example 3).

Statistical Data Analyses Human data was analyzed using IBM SPSS Statistics version 20. General Linear Models for repeated measures were applied with the placebo condition included as contrast. Statistical outcomes for Tests of Within-Subjects Effects and Tests of Within-Subjects Contrasts were regarded for immediate and delayed free recall scores and for the summed immediate recall score (i.e. immediate 1+immediate 2+immediate 3). The factor Treatment (4 levels; placebo, roflumilast 100 mcg, roflumilast 300 mcg and roflumilast 1000 mcg) was included as a within subjects factor. For the analysis of the EEG data, the factor Channel (5 levels; Fz, FCz, Cz, CPz, and Pz) was included as a second within subjects factor. Peak and latency values of three memory related ERP's were analysed; i.e. P300, N400 and P600. In case of significant findings (p<0.05) post-hoc t-tests were performed to reveal which of the five midline electrodes contributed to the effect.

Results

Figure 2:
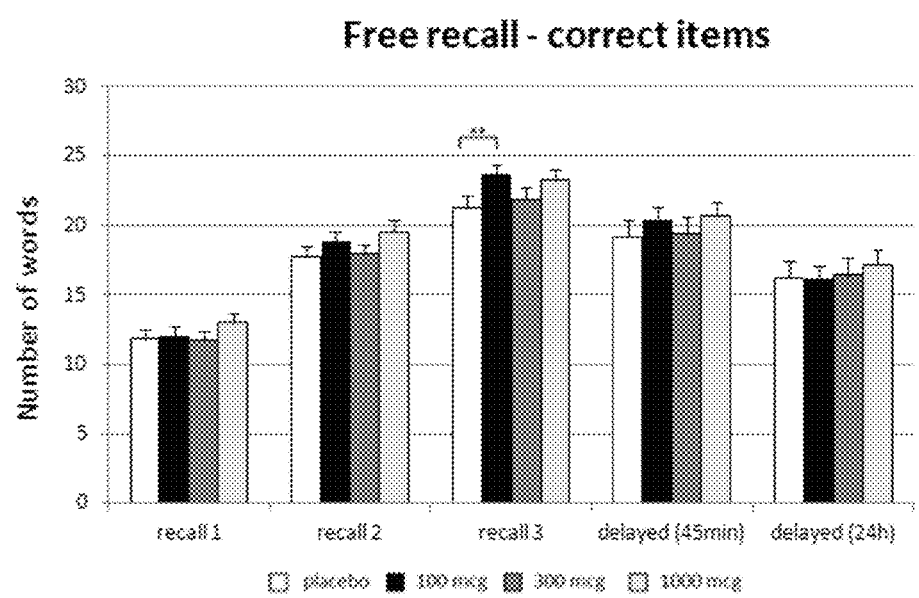
FIG. 2 is a graph illustrating the number of words correctly remembered by healthy adult subjects during the Verbal Learning Task (VLT) following administration of various doses of roflumilast ($1^{st}$, $2^{nd}$, and $3^{rd}$ recall, 45 min delayed and 24 h delayed).

Low dose roflumilast (i.e., 100 mcg) but not higher doses (i.e., 300 and 1000 mcg) showed significant increase in the number of correct words recalled only after the $3^{rd}$ trial of VLT (FIG. 2).

As shown in FIG. 2, VLT analyses using a General Linear Model for repeated measures, with the placebo condition included as contrast demonstrated that roflumilast caused increase in number of correct words reached to statistically significant levels after only 100 mcg dose and observed only at $3^{rd}$ recall (tests of within subjects contrasts: 100 mcg vs. placebo: **p=0.004; 300 mcg vs. placebo: p=0.624; 1000 mcg vs. placebo: p=0.137).

Figure 3:
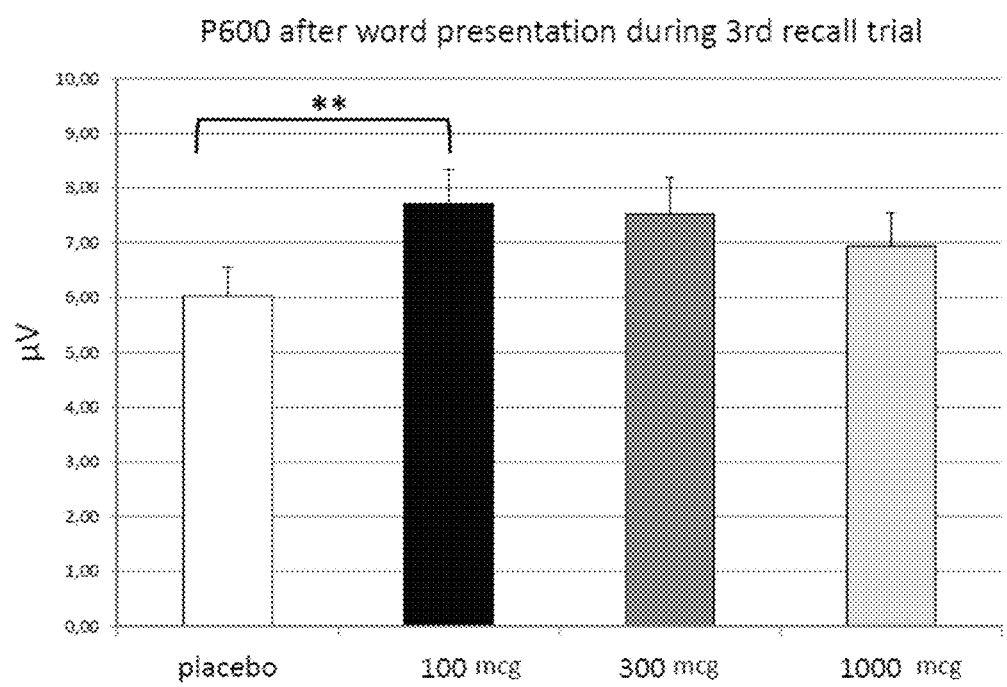
FIG. 3 illustrates quantitative bar graph analysis of the results of the electroencephalography data depicting the effect of roflumilast on Event-Related Potentials during the VLT ($3^{rd}$ trial only).

In parallel, the corresponding EEG measurements revealed that ERP, P600 demonstrated increased amplitude with low dose Roflumilast (i.e., 100 mcg) but not with higher doses (i.e., 300 and 1000 mcg) (FIG. 3).

FIG. 3 shows EEG co-measurements using a General Linear Model for repeated measures, with the placebo condition included as contrast during VLT $3^{rd}$ recall and demonstrated that roflumilast 100 mcg caused statistically significant induction in mean peak values at the Pz electrode (tests of Within Subjects Contrast, factor Treatment: placebo—100 mcg: p=0.048; placebo—300 mcg: p=0.109; placebo—1000 mcg: p=0.440). Post-hoc paired sample t-tests were performed to specify the effects for the 5 midline electrodes in the 100 mcg condition as compared to placebo: Fz: p=0.465; FCz: p=0.315; Cz: p=0.015; CPz: p=0.025; Pz: p=0.002. The values in the figure refer to the mean peak values measured at the Pz electrode, i.e. **p=0.002.

FIGS. 2 and 3 do show some effect also for the 300 mcg and 1000 mcg dose. Analysing the roflumilast/roflumilast-N-oxide blood plasma levels of the treated healthy volunteers, it was revealed that some individuals in the 300 mcg as well as in the 1000 mcg dose group exhibited plasma concentration levels comparable to the plasma concentration levels of the individuals from the 100 mcg dose group. If the response is dependent on a specific targeted plasma concentration level range, then individuals with similar plasma concentration levels would be expected to show similar responses. Most likely, the reformulated roflumilast capsules used in the trial lead to some variability in the absorption profile of roflumilast in the 20 healthy adults. Therefore the effect of the 300 mcg and the 1000 mcg dose actually is probably to a certain extent lower than shown in FIGS. 2 and 3.

In the VLT, Roflumilast was effective at the single dose of 100 mcg in improving number of correct words recalled (average 2.5 words). This is a meaningful effect considering the age group and the education levels of the participants (i.e., young adult college students). Based on these results, one can expect to see larger effect with Roflumilast in elderly subjects with naturally occurring cognitive decline. Further, during the recall analyses, increased brain activity was observed at P600 only with low dose, 100 mcg Roflumilast. This finding further supports the fact that the improvement observed on behavioural outcome (i.e., recalling more correct words) is a reflection of enhancement in brain activity captured and measured by EEG/ERPs.

No statistically significant differences were found between placebo and drug treatment in the Spatial Memory Task, the Stroop task and the Continuous Performance task.

The results of this study, taken together with the rodent data, indicate that low doses but not high doses (such as the approved once daily dose for the treatment of severe COPD; 500 mcg) of Roflumilast are effective in improving cognitive functioning (e.g., memory deficits). Low dose Roflumilast, with better side effect and tolerability profile offers more suitable treatment for the cognitive impairment associated with aging (dementia, Mild Cognitive Impairment (MCI) and Alzheimer's disease) as well as with Schizophrenia.

Example 3

Analysis of Cognitive Effects of Roflumilast on Age-related Memory Impairment

The primary objective of this study is to examine any improvement, following roflumilast administration, in memory of elderly subjects having (a) normal age-related memory impairment or (b) having enhanced age-related memory impairment, by means of behavioral tasks.

The secondary objective of this study is to assess the effects of roflumilast on the electrophysiological correlates of memory and cognition.

Method

The study is conducted according to a double-blind, placebo-controlled, four-period cross-over design. Forty healthy subjects, both male and female within an age range of 60 to 80 years are planned to be included in the study in 2 groups: 1) 20 subjects with a memory performance between 1-2 Standard Deviation below the average for their age, gender, and educated level (Impaired Elderly) and 2) 20 subjects with age (±3 years), gender, and educational level matched (in order to speed up the study matching was stopped after the interim analysis) with an average memory performance between 0.5 Standard Deviation below and 0.5 Standard Deviation above from normative values (Healthy Elderly). Classification in terms of impaired or healthy elderly will be determined by a one-off testing of memory performance using the Rey Verbal Learning Task (Rey A; L'examen psychologique dans les cas d'encephalopathy traumatique 1958 Paris; Presses Universitaire de France; or Van der Elst et al; J Int Neuropsychol Soc 2005, 11 (3), pp 290-302) according to fully standardized procedures as applied in The Maastricht Aging Study (Jolles et al; Maastricht Aging Study; determinants of cognitive aging; Maastricht, The Netherlands, Neuropsych Publishers 1995). Normative data for each individual subject will be derived also from the Maastricht Aging Study using the regression formula as described by Van der Elst et al (Van der Elst et al; J Int Neuropsychol Soc 2005, 11 (3), pp 290-302).

All subjects within their corresponding groups (either Healthy Elderly n=20 or Impaired Elderly n=20) will be randomized in a double blind fashion to 1 of 4 treatment sequences, each sequence consisting of the following periods: A) Placebo+placebo; B) Roflumilast 100 mcg+placebo; C) Roflumilast 250 mcg+placebo and D) Roflumilast 1000 mcg (500+500 mcg) according to a computer-generated allocation schedule in a cross-over design. Between each of the four treatment sequences there will be a 12 days washout period.

Cognitive status will be quantified using computerized cognitive battery, a validated tool for measuring the cognitive impairment in humans. The battery will consist of: VLT, Spatial Memory Task (SMT), Stroop Task, and Bond-Lader Visual Analogue Scales (BL-VAS).

Brain electrical activity changes will be quantified with EEG battery tests. The EEG battery tests will be administered to all subjects during VLT, SMT, Stroop as well as for sensory gating and Novelty oddball task.

Overview of testing day for each Treatment Period (Day 1 and 2) is given below:

| Time (min); Relative to dosing | Activity |
| --- | --- |
| −5 | BL-VAS |
| 0 | Dosing (A, B, C or D) |
| 55 | Baseline EEG recording (5 min; eyes closed) |
| 60 | VLT Immediate recall, 3 trials (10 min) |
| 70 | Pharmacokinetic (PK) blood sampling |
| 75 | SMT immediate recall (10 min) |
| 85 | Stroop task (10 min) |
| 95 | Sensory gating (10 min) |
| 105 | BL-VAS (5 min) |
| 110 | VLT Delayed recall (3 min) and recognition (3 min) |
| 120 | SMT delayed recall (5 min) |
| 125 | Novelty Oddball task (10 min) |
| 135 | EEG recording, resting state (5 min, eyes closed) |
| 140 | PK blood sampling |
| 145 | Participants return home |
| Next Day | |
| 1430 | Participants arrive |
| 1435 | BL-VAS (5 min) |
| 1440 (24 h) | VLT Delayed recall (3 min) and recognition (3 min) |
| 1450 | SMT picture recognition and delayed recall (10 min) |
| 1460 | Stroop task (10 min) |
| 1470 | PK Blood sampling |

Verbal learning task (VLT) The Rey VLT as modified by Riedel and colleagues (Riedel, Klaasen et al, Psychopharmacology (Berlin) 1999 Vol 141(4) pp 362-369) is used. This modified VLT maximizes the possibility of measuring enhancement rather than only impairment, by means of prolonging the list. The test consists of a list of 30 monosyllabic words (18 nouns and 12 adjectives). The words are shown on a computer screen for 1 second. Three trials with the same item sequence are presented. Each trial ends with a free recall of the words (immediate recall). Forty-five minutes after the first exposure, the subject is asked to recall as many words as possible (delayed recall). Subsequently, a recognition test is presented, consisting of 15 former words and 15 new but comparable words (distracters). The words are shown on a computer screen for 2 seconds and subjects are asked to rate whether they were presented in the learning trial by a "yes/no" response. The inter-word interval is 2 seconds. 24 Hours after the immediate recall, subjects will return to the lab for a second delayed recall and recognition. The remaining 15 old words and 15 new words will be presented during recognition. EEG will be recorded during the immediate recall and the first recognition test on the test day. No EEG recording will be performed during the first delayed recall and recognition at the 24 h measurement. The number of words correctly recalled will be collected during the three immediate learning trials (first, second, third and total) delayed, and recognition periods. The number of words correctly recalled in the learning trials is summed to yield the total immediate free recall score.

Spatial memory task (SMT) The spatial memory task assesses spatial memory and is based on the object relocation task by Postma and colleagues (Kessels, Postma et al, Behav Res Methods Instrum Comput. 1999, Vol 31(3) pp 423-428). It consists of one immediate and two delayed conditions. In the immediate condition, a set of 10 pictures will be presented one by one on different locations within a white square on a computer screen. All pictures are everyday, easy-to-name objects, presented in gray scale (±3.5×5 cm). Each picture will be presented for 2000 msec with an interstimulus interval of 1000 msec. This will be followed by a "relocation" part, which consists of the presentation of a picture in the middle of the screen, followed by a "1" and a "2" being presented on two different locations. The participants' task is to decide where the picture was originally presented, in location "1" or location "2". The "1" and "2" will remain on the screen until the participant responds. After relocation, which is accomplished by a button press, the next picture will be presented followed by a "½" choice option. This continues until all 10 pictures have been relocated. Thereafter, the next set of 10 pictures will be presented. A total of 6 sets of 10 pictures are displayed. Forty-five minutes later, subjects will perform the first delayed version. The original locations are not presented again. Subjects immediately start with the relocation part of the task.

Twenty-four hours after the immediate condition, subjects will return to the lab and perform the task again. This time, the SMT will include a recognition phase. They are shown 60 old pictures (i.e. from the SMT task) and 60 new pictures (i.e. not seen before in the SMT task), in 6 blocks of 20 pictures each (each block contains 10 old and 10 new pictures). The subjects have to rate within 2 seconds whether they were presented with these pictures in the learning trials by a "yes/no" response. If the subject indicates that they have seen a picture before, they are again presented with a "1" and a "2" on two different locations (regardless of the correctness of their response). Once more, they have to decide where the picture was originally presented in location "1" or location "2". The "1" and "2" will remain on the screen until the subject responds. If the subject indicates that the picture presented is new, no reply with regard to the original location has to be made. The space bar can be pressed instead, and the next picture will appear after a brief interval requiring the next "yes/no" response. As with the other tests, the EEG will be recorded during this task and this will later be analysed. No EEG will be recorded during the 24h-measurement. The number of correctly localized items will be collected during the immediate and the two delayed periods.

Stroop task The Stroop task is well known for its ability to induce interference, and assesses response inhibition and focused attention. In this task, colour names are printed in coloured ink; in the congruent category, the colour name and the colour of the ink are the same, in the incongruent category they are not. The subjects have to name the colour of the ink, not the words themselves. However, because of the urge to read the printed words (even if one is asked to ignore them) interference occurs. Since the printed words and ink colour differ in the incongruent category, interference is larger in this category than in the congruent category; this is called the "Stroop effect" and is known to remain even after extended practices (Gazzaniga, Ivry et al 2002, Cognitive neuroscience: The biology of the mind, W.W. Norton & Company, Inc.). The colours used in this task are blue, red, green and yellow. The colour of the ink has to be named by pressing one out of four buttons, which each represent one of the colours. The main performance measures are the reaction time (RT) and the number of errors. The Stroop task will also be presented at the 24 h measurement. EEG will be recorded during the first but not the second presentation of the task (i.e. no EEG at the 24 h measurement) and it will be analysed similarly to the EEG recorded during VLT.

Sensory gating Subjects will be presented with one type of auditory stimuli, a click with a duration of 3 ms, constructed from a 1000 Hz tone. Clicks will be presented in pairs with an interval of 500 ms between the first (S1) and the second (S2) click. The interval between click pairs will be random between 6 and 10 s and the intensity of the click is around 60 dB. The subjects will be asked to sit quietly and listen to the tones. EEG will be recorded during this task, of which ERPs will be calculated offline. The most important ERP component is the P50, which is usually reduced in amplitude to the second as compared to the first click. By calculating the ratio (S2/S1), an indication of the amount of gating can be obtained.

Novelty oddball task The novelty oddball task assesses involuntary attention processes. It is a passive paradigm, in which three types of auditory stimuli are presented while the subject watches a silent movie/cartoon and ignores the stimulation. The stimuli consist of frequent standard, infrequent deviant and infrequent novel stimuli. The standard and deviant stimuli will be 500 Hz and 750 Hz tones with two upper harmonic components (1000 and 1500, 1500 and 2250 Hz, respectively). The intensity of the first and second harmonic components is decreased compared to the fundamental by 3 and 6 dB, respectively. The use of those stimuli will be counterbalanced between subjects, but will remain constant for the different measurements within subjects. Novel stimuli consist of three stimulus categories of 20 different sounds, namely animal, human, and mechanical sounds. The deviant and novel stimuli will each be presented in 12.5% of the trials. All sounds have duration of 300 ms with 10 ms rise and fall times and will be presented with a 1000 ms stimulus onset asynchrony and equal intensities to both ears using a headphone. No behavioral measures will be recorded. ERPs will be recorded, from which the N100 will be analysed. Furthermore, the response to the standard will be substracted from the deviant and novel stimuli, which enables the visualization of the mismatch negativity and P3a components, the latter being a novelty response. The amplitudes and latencies of these components will be compared between the deviant-standard and novel standard responses. The P3a component measures the involuntary switch to novel stimuli, whereas the mismatch negativity is a measure of sensory memory.

Bond-Lader Visual Analogue Scales (BL-VAS): The BL-VAS (Bond A and Lader M, 1974; Br J Med Psychol Vol 47, pp. 211-218) will be used in order to assess alertness, calmness, and contentedness. BL-VAS consists 16 100 mm visual analogue scales anchored by antonyms (e.g. Alert-Drowsy, Lethargic-Energetic; etc) and be applied on testing Day 1 and 2 of each treatment period.

For the EEG measurements, an EEG cap will be used to place a set of 32 EEG electrodes according to the international 10-20 system. A reference and a ground will be placed at the linked mastoids and at the forehead, respectively. Eye movements will be detected by horizontal and vertical electro-oculogram (EOG) recordings. Before electrode attachment, the positions will be slightly scrubbed with a gel in order to provide a good measurement. Both EEG and EOG will be filtered between 0.01 and 100 Hz and sampled at 500 Hz. Offline, the EEG will be checked for EOG activity and other artifacts. The EEG that contains artifacts will be excluded from analysis. ERPs will be extracted by averaging the responses within an epoch of 100 ms before and 1000 ms after stimulus onset. Separate averages will be made for correct and incorrect responses within a task and for different trial types. With regard to the VLT, the following measures will be used. ERPs will be calculated from the thirty words presented during each of the three immediate recall trials separately. Additionally, ERP's for both old and new word, as presented during the recognition paradigm at 45 min will be calculated. Primarily, the P300, N400 and P600 components will be analysed for both tasks.

Expected outcome: It is expected that in this elderly study population, in particular in the group of subjects with an enhanced age-associated memory impairment, the signals seen in the young healthy subjects in the study of example 2, will be confirmed and will at the same time be more pronounced, i.e. (1) efficacy of low dose roflumilast and (2) inefficacy of the single administration dose (1000 mcg) correlating with the repeated administration dose of roflumilast approved for the treatment of severe chronic obstructive pulmonary disease (500 mcg) will be confirmed.

Interim Analysis

An interim analysis has been performed based on the data of 9 subjects of the Impaired Elderly group and 4 subjects of the Healthy Elderly group. For this purpose, cognitive battery test scores (VLT, SMT, Stroop task and BL-VAS) and concentrations of roflumilast and roflumilast-N-oxide in plasma have been analysed and summarized by dose over each scheduled sampling time using descriptive statistics.

Results of Interim Analysis

The results are based on a pooled interim analysis from 9 subjects of the Impaired Elderly group and 4 subjects of the Healthy Elderly group who have already completed the study.

In the present study, subjects of the Healthy Elderly group remembered 10 words after 3 learning trials on a 30 words list task, whereas subjects of the Impaired Elderly group remembered 7.9 words after 3 learning trials on the 30 word list task.

Figure 4:
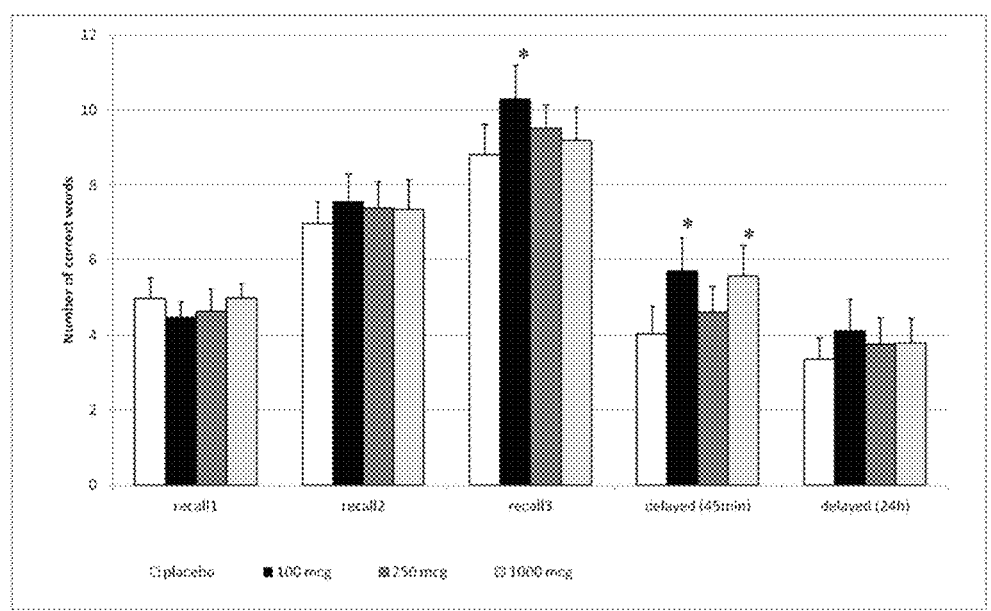
FIG. 4 is a graph illustrating the number of words correctly remembered by 60 to 80 years old subjects during the Verbal Learning Task (VLT) following administration of various doses of roflumilast ($1^{st}$, $2^{nd}$, $3^{rd}$ recall, 45 min delayed and 24 h delayed).

Though the interim analysis population was small, there were effects indicative of activity. Compared to placebo, low dose roflumilast (i.e., 100 mcg) but not higher doses (i.e., 250 and 1000 mcg) showed a statistically significant ($p<0.05$) increase in the number of correct words immediately recalled (i.e., 1.5 words) after the 3rd trial of VLT (FIG. 4). Compared to placebo, low and high dose roflumilast (i.e., 100 and 1000 mcg, respectively) but not middle dose (i.e., 250 mcg) showed a statistically significant ($p<0.05$) increase in the number of correct words (i.e., 1.7 and 1.6 words, respectively) recalled after 45 min delayed recall trial of VLT (FIG. 4). Also, the subjects reported significantly higher (subjective) alertness in comparison with placebo only at 45 min after the low dose, based on BL-VAS scores.

No statistically significant differences were detected between placebo and drug treatment in the Spatial Memory Task, and Stroop task.

The exposure to roflumilast and roflumilast N-oxide were consistent with those previously reported.

Following a single low dose of roflumilast (100 mcg), an improvement in the number of correct words immediately recalled (i.e., 1.5 words) was observed. As with immediate recall, a similar improvement seen in delayed recall appears to confirm its clinical meaning. The placebo-corrected fold-improvement was 1.16 in the present interim data of the elderly study. This was consistent with the fold-improvement of 1.12 in the healthy volunteer study, though the absolute word improvement on the 3rd trial from 8.81 to 10.28 words in elderly subjects was smaller than that of 21.25 to 23.7 words on the 3rd trial in young volunteers in the previous study (Example 2). Taken together, the interim data analysis of the elderly subjects supports the finding that low dose roflumilast enhances episodic memory performance observed in young volunteers, thereby adding considerable weight to its potential usefulness in prodromal dementia (mild cognitive impairment (MCI)).

The results of this study, taken together with the results in healthy adults and the rodent data, indicate that low doses of roflumilast may be effective in improving cognitive functioning (e.g., memory deficits). Low dose roflumilast, with better side effect and tolerability profile compared to the approved once daily dose for the treatment of severe COPD (500 mcg) offers more suitable treatment for the cognitive impairment associated with aging [dementia, Mild Cognitive Impairment (MCI) and Alzheimer's disease] as well as with Schizophrenia.

As shown in FIG. 4, VLT analyses using a General Linear Model for repeated measures, with the placebo condition included as contrast demonstrated that roflumilast caused increase in number of correct words reached to statistically significant levels for 3rd recall at 100 mcg and delayed (45min) recall at 100 and 1000 mcg (Tests of within subjects contrasts: 3rd recall: 100 mcg vs. placebo: *$p=0.024$; 250 mcg vs. placebo: $p=0.245$; 1000 mcg vs. placebo: $p=0.527$; Delayed (45 min) recall: 100 mcg vs. placebo: *$p=0.015$; 250 mcg vs. placebo: $p=0.351$; 1000 mcg vs. placebo: *$p=0.021$).

Example 4

Analysis of Cognitive Improvement Effects of Roflumilast on Memory Performance in Rats The objective of this study is to evaluate the efficacious dose range of roflumilast with regard to cognitive improvement effects by using scopolamine induced memory deficit on object memory performance in male Wistar rats. Memory acquisition processes are investigated using the object recognition test (ORT).

Methods

Maintenance of Animals: Sixteen 3-4 month old male Wistar rats (Charles River, Sulzfeld, Germany) were used for the study. All animals were housed individually in standard green line Tecniplast IVC cages on stardust bedding. The animals were housed on a reversed 12/12 h light/dark cycle (lights on from 07:00 pm to 07:00 am) and had free access to food and water. The rats were housed and tested in the same room. A radio, playing softly, provided background noise in the room. All testing was performed between 09:00 am and 06:00 pm.

Preparation of Compounds: Drugs were prepared daily, except as indicated otherwise. Roflumilast (Takeda, Konstanz, Germany, MW 403.21) was dissolved in 98% methylcellulose solution (0.5% methylcellulose) and 2% Tween 80. Roflumilast in doses of 0 (vehicle), 0.0001, 0.0003, 0.001, 0.003, 0.01 and 0.03 mg/kg was administered intraperitoneally (ip, injection volume 1 ml/kg). Scopolamine (in form of scopolamine hydrobromide) was dissolved in saline (0.9% NaCl). Scopolamine hydrobromide was administered intraperitoneally at a dose of 0.1 mg/kg (ip, injection volume 1 ml/kg). Scopolamine and roflumilast were administered 30 min before T1.

Object Recognition Task in Rats: The ORT was performed as described elsewhere (Ennaceur and Delaceur, 1988, Behav Brain Res, Vol 31, pp 47-59; Akkerman et al; 2012, Behav Brain Res, Vol 232, pp 335-347). The apparatus consisted of a circular arena, 83 cm in diameter. The back half of the 40 cm high wall was made of grey PVC and the front was made of transparent PVC. Fluorescent red tubes and a light bulb provided a constant illumination of about 20 lux on the floor of the apparatus. The light intensity was equal in the different parts of the apparatus.

Two objects were placed in symmetrical positions at the mid-line between the gray and transparent halves of the arena, about ten centimeters away from wall. Four different sets of objects were available: 1) a standard 1 L brown transparent glass bottle (diameter 10 cm, height 22 cm) filled with water, 2) a metal cube (10.0×5.0×7.5 cm) with two holes (diameter 1.9 cm), 3) a cone consisting of a gray PVC base (maximal diameter 18 cm) with a collar on top made of brass (total height 16 cm), and 4) an aluminium cube with a tapering top (13.0×8.0×8.0 cm). Objects were presented to the animals in a balanced manner to avoid object or place biases. Rats were unable to displace the objects.

A test session comprised two trials, each with durations of 3 min. During the learning trial (T1) the apparatus contains two identical objects (object a1 and a2). Rats were always introduced into the apparatus with their nose towards the transparent wall segment (i.e. facing outwards to the front of the arena). Subsequently, rats were put back in its home cage for a 1 h interval. After the retention interval, rats were put back into the arena for the learning trial (T2). In T2, the two objects from T1 were replaced by one identical copy (a3) and a different novel object (b). The times spent in exploring each object during T1 and T2 were recorded manually on a personal computer.

Exploration was defined in the following manner: directing the nose to the object at a distance of no more than 2 cm and/or touching the object with the nose. Sitting on the object was not considered as exploratory behavior. In order to avoid the presence of olfactory cues, the objects were thoroughly cleaned with a 70% ethanol solution before each trial.

Experimental Procedure:

Prior to compound testing, the animals were handled for 5 min on 2 consecutive days and allowed to explore the ORT arena, also for 5 min. Subsequently, the animals were accustomed to the complete ORT testing procedure without receiving any injection. As soon as the animals showed good discrimination performance at a 1 h interval, the testing for the roflumilast dose response study was started. First, the saline/vehicle and scopolamine (0.1 mg/kg)/vehicle conditions were tested to verify that the cholinergic deficit model effectively impaired object memory. Next, a dose-response curve was created by testing several doses (0.0001, 0.0003, 0.001, 0.003, 0.01 and 0.03 mg/kg) of roflumilast in combination with scopolamine. Table 3 below shows a schematic overview of the names and details of the different conditions in the dose-response study.

TABLE 3

Experimental conditions of the roflumilast dose-response study

| Condition Name | Dose Scopolamine (mg/kg) | Dose Roflumilast (mg/kg) |
|---|---|---|
| vehicle | 0 (vehicle) | 0 (vehicle) |
| scopolamine | 0.1 | 0 (vehicle) |
| 0.0001 mg/kg | 0.1 | 0.0001 |
| 0.0003 mg/kg | 0.1 | 0.0003 |
| 0.001 mg/kg | 0.1 | 0.001 |
| 0.003 mg/kg | 0.1 | 0.003 |
| 0.01 mg/kg | 0.1 | 0.01 |
| 0.03 mg/kg | 0.1 | 0.03 |

Scopolamine and roflumilast were administered 30 min before T1. The retention time between T1 and T2 was 1 h.

Statistical Analysis:

The readout parameters of the object recognition task are the times that rats spent on exploring each object during T1 and T2. The exploration time (in seconds) of each object during T1 are presented as "a1" and "a2". The time spent in exploring the familiar and the new object in T2 are presented as "a" and "b", respectively. Using this information, the following variables are calculated: e1, e2 and d2 (see Table 4 below). The d2 index is a relative measure of discrimination corrected for exploratory activity and has been shown not to be correlated with e1 and e2 (Akkerman et al, 2012, Behav Brain Res Vol 232, pp 317-322). The d2 index can range from −1 to 1. A significant difference from zero indicates that rats remembered the objects from T1 and a difference from the vehicle condition signifies an actual memory improvement. Of note, rats require a minimum amount of exploration in order to show reliable memory performance (Akkerman et al, 2012, Behav Brain Res Vol 232, pp 335-347). Therefore, animals are removed from the analysis if they spend less than 6 sec or 9 sec exploring the objects during T1 and T2, respectively. In the present study, none of the animals had to be excluded.

TABLE 4

Object recognition task (Read-out Measures and their calculations)

| Trial | Exploration time (sec) | Discrimination Index |
|---|---|---|
| T1 | e1 = a1 + a2 | — |
| T2 | e2 = a + b | d2 = (b − a)/e2 |

One sample t-statistics were performed to assess whether the d2 index for each treatment condition was significantly different from zero (chance level). However, comparison of the value of d2 with the value zero with no variance is not the most suitable way of analyzing object recognition since there is an increased chance of making a type I error. For this reason, treatment conditions were also compared using one-way ANOVA. In case of significant differences between treatment conditions, post-hoc analyses were performed using Bonferroni t-tests to compare each treatment to the vehicle condition. All statistical analyses were performed using an α of 0.05.

Results: The effects of roflumilast on a scopolamine induced memory deficit in the ORT The results of the dose-response experiment with roflumilast in the scopolamine induced memory deficit are summarized in Table 5. One way ANOVA revealed no significant differences between treatment conditions in the level of exploration in T1 (e1: $F(7, 120)=1.09$, n.s.) and T2 (e2: $F(7,120)=0.82$, n.s.)

TABLE 5

Mean values (±SEM) of the different ORT measures in the roflumilast dose response study

| Condition | e1 (sec) | e2 (sec) | d2 | n |
|---|---|---|---|---|
| vehicle | 23.88 (2.31) | 25.31 (1.84) | 0.43 (0.05) ### | 16 |
| scopolamine | 20.99 (2.17) | 25.03 (2.18) | 0.01 (0.08) | 16 |
| 0.0001 mg/kg | 24.18 (1.56) | 28.13 (2.17) | 0.05 (0.05) | 16 |
| 0.0003 mg/kg | 19.40 (1.62) | 24.10 (1.88) | 0.16 (0.06) # | 16 |
| 0.001 mg/kg | 19.95 (1.38) | 22.88 (2.14) | 0.27 (0.06) ### | 16 |
| 0.003 mg/kg | 22.38 (1.09) | 23.94 (1.28) | 0.43 (0.06) ### | 16 |
| 0.01 mg/kg | 22.54 (1.63) | 27.20 (1.72) | 0.34 (0.06) ### | 16 |
| 0.03 mg/kg | 20.44 (1.64) | 26.10 (2.06) | 0.30 (0.07) ### | 16 |

One sample t-tests were performed on the d2 measures, a significant difference from zero (indicated by hash-signs; #: $p < 0.05$; ###: $p < 0.001$) indicates that the animals remembered the object from T1.

One sample t-tests were used to compare the d2 of the different treatment to zero. It was found that the d2 values of all conditions were significantly higher than zero, except the d2 values of the scopolamine and 0.0001 mg/kg conditions (see Table 5). One-way ANOVA revealed significant differences in d2 between treatment conditions ($F(3,81)=6.67$, $p<0.001$). Post-hoc analyses with Bonferroni t-tests showed that the vehicle, 0.003 mg/kg, 0.01 mg/kg and 0.03 mg/kg conditions has a significantly higher d2 value compared to the scopolamine condition. On the other hand, only the scopolamine and 0.0001 mg/kg conditions were significantly lower compared to the vehicle condition.

Taken together these data indicate that roflumilast was able to fully restore memory function at doses of 0.003 mg/kg and higher whereas animals treated with 0.0003 mg/kg and 0.001 mg/kg only showed intermediate memory improvement, i.e. were only different from zero. The dose of 0.0001 mg/kg roflumilast had no effect on memory performance.

Figure 5:
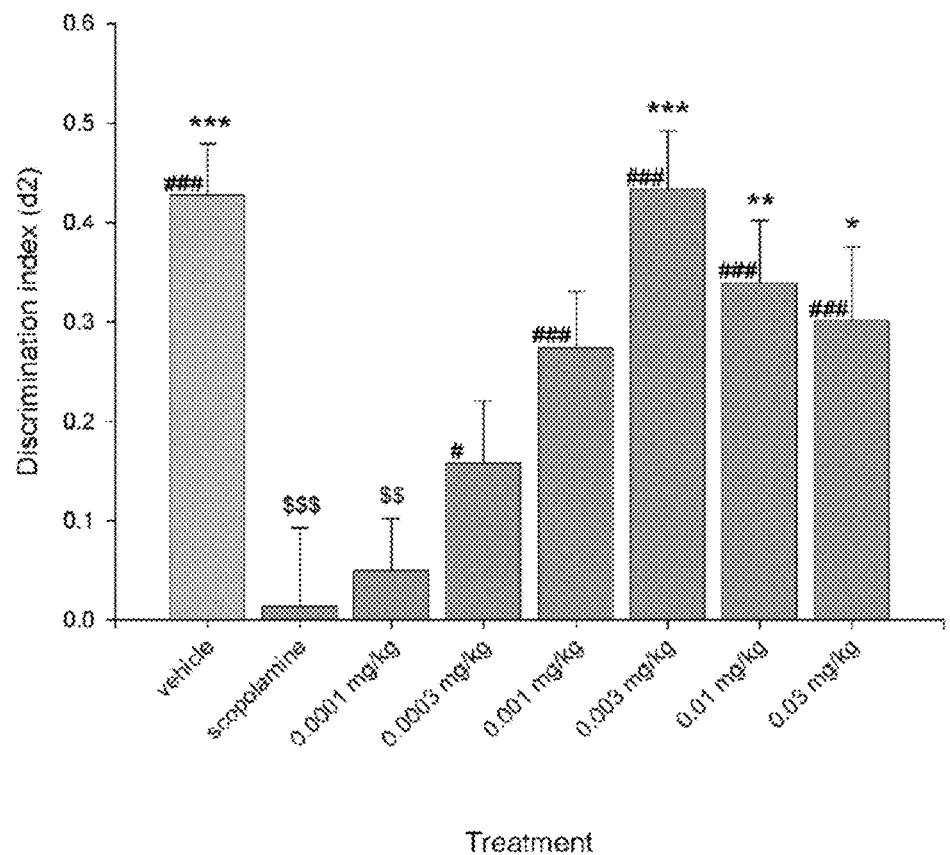
FIG. 5 illustrates the effects of different roflumilast doses on a scopolamine induced memory deficit in the Object recognition task in male Wistar rats.

The effects of the different doses of roflumilast on object memory performance are graphically presented in FIG. 5.

In FIG. 5 is shown the average d2 value and SEM of each treatment condition in the roflumilast dose response study. The discrimination index (d2) is indicated on the y-axis and the different treatment conditions are shown on the x-axis. Hash signs indicate a difference from zero (#: $p<0.05$; ###: $p<0.001$), a difference from the vehicle condition is indicated with dollar signs ($$: $p<0.01$; $$$: $p<0.001$) and a difference from the scopolamine condition is indicated with asterisk (*: $p<0.05$; : $p<0.01$; *: $p<0.001$).

The invention claimed is:

1. A method of treating mild cognitive impairment in a human in need of such treatment, the method comprising:
    administering to the human suffering from mild cognitive impairment a phosphodiesterase 4 inhibitor selected from the group consisting of roflumilast, a pharmaceutically acceptable salt of roflumilast, roflumilast-N-oxide and a pharmaceutically acceptable salt of roflumilast-N-oxide,
    wherein the phosphodiesterase 4 inhibitor is administered to the human at a daily dose consisting of between 50 mcg and 100 mcg.

2. The method of claim 1, wherein the phosphodiesterase 4 inhibitor is selected from the group consisting of roflumilast and a pharmaceutically acceptable salt of roflumilast.

3. The method of claim 1, wherein the phosphodiesterase 4 inhibitor is selected from the group consisting of roflumilast-N-oxide and a pharmaceutically acceptable salt of roflumilast-N-oxide.

4. The method of claim 1, wherein the phosphodiesterase 4 inhibitor is roflumilast.

5. The method of claim 1, wherein the phosphodiesterase 4 inhibitor is roflumilast-N-oxide.

6. The method of claim 1, wherein the phosphodiesterase 4 inhibitor is administered at a daily dose of 50 mcg or 100 mcg.

7. The method of claim 1, wherein the phosphodiesterase 4 inhibitor is roflumilast and wherein the phosphodiesterase 4 inhibitor is administered at a daily dose of between 50 mcg and 100 mcg.

* * * * *